(12) United States Patent
Kumamoto et al.

(10) Patent No.: US 7,749,357 B2
(45) Date of Patent: Jul. 6, 2010

(54) MOLDED SHEET

(75) Inventors: Yoshiaki Kumamoto, Tochigi (JP);
Masataka Ishikawa, Tochigi (JP);
Kunio Matsui, Tochigi (JP)

(73) Assignee: KAO Corporation, Tokyo (JP)

( * ) Notice: Subject to any disclaimer, the term of this patent is extended or adjusted under 35 U.S.C. 154(b) by 814 days.

(21) Appl. No.: 10/534,047

(22) PCT Filed: Jun. 11, 2003

(86) PCT No.: PCT/JP03/07425

§ 371 (c)(1),
(2), (4) Date: Nov. 22, 2005

(87) PCT Pub. No.: WO2004/041135

PCT Pub. Date: May 21, 2004

(65) Prior Publication Data

US 2006/0151136 A1    Jul. 13, 2006

(30) Foreign Application Priority Data

Nov. 8, 2002    (JP)    ............................... 2002-325079

(51) Int. Cl.
*A61F 7/08* (2006.01)
*D21J 3/00* (2006.01)

(52) U.S. Cl. .................. 162/218; 162/135; 162/158; 162/181.9; 162/184; 428/156; 428/172; 126/200; 126/263.02

(58) Field of Classification Search .......... 162/134–135, 162/158, 183–184, 181.1–181.9, 204–205, 162/123–133, 141, 149, 145, 147, 218, 146; 126/204, 263.01–263.02; 428/156, 172, 428/537.5; 442/334, 352
See application file for complete search history.

(56) References Cited

U.S. PATENT DOCUMENTS

| | | | | | |
|---|---|---|---|---|---|
| 1,991,824 | A | * | 2/1935 | Snyder | 162/10 |
| 2,993,816 | A | * | 7/1961 | Blake | 428/338 |
| 3,022,213 | A | * | 2/1962 | Pattilloch et al. | 162/138 |
| 4,383,890 | A | * | 5/1983 | Oshima et al. | 162/157.6 |
| 4,416,800 | A | * | 11/1983 | Abe et al. | 502/159 |
| 4,904,343 | A | * | 2/1990 | Giglia et al. | 162/145 |
| 5,240,561 | A | * | 8/1993 | Kaliski | 162/138 |
| 5,503,849 | A | * | 4/1996 | Bilodeau | 428/448 |
| 5,975,074 | A | * | 11/1999 | Koiso et al. | 126/204 |
| 6,127,294 | A | * | 10/2000 | Koiso et al. | 442/327 |
| 6,133,170 | A | * | 10/2000 | Suenaga et al. | 442/334 |
| 6,494,991 | B1 | * | 12/2002 | Palmer et al. | 162/181.6 |
| 6,740,373 | B1 | * | 5/2004 | Swoboda et al. | 428/34.2 |
| 6,843,887 | B2 | * | 1/2005 | Kumada et al. | 162/146 |
| 6,974,470 | B2 | * | 12/2005 | Tsunakawa et al. | 607/109 |
| 7,353,820 | B2 | * | 4/2008 | Kumamoto et al. | 126/204 |
| 7,625,464 | B2 | * | 12/2009 | Matsui et al. | 162/218 |
| 2002/0081930 | A1 | * | 6/2002 | Jackson et al. | 442/416 |
| 2002/0100568 | A1 | * | 8/2002 | Covarrubias | 162/181.4 |
| 2002/0153111 | A1 | * | 10/2002 | Kumada et al. | 162/157.3 |
| 2002/0155281 | A1 | * | 10/2002 | Lang et al. | 428/337 |
| 2004/0045690 | A1 | * | 3/2004 | Eto et al. | 162/225 |
| 2005/0028806 | A1 | * | 2/2005 | Kumamoto et al. | 126/263.02 |
| 2005/0192653 | A1 | * | 9/2005 | Tsunakawa et al. | 607/109 |
| 2006/0151136 | A1 | * | 7/2006 | Kumamoto et al. | 162/158 |
| 2006/0276863 | A1 | * | 12/2006 | Kumamoto et al. | 607/96 |
| 2007/0020412 | A1 | * | 1/2007 | Kumamoto et al. | 428/34.2 |
| 2007/0110790 | A1 | * | 5/2007 | Igaki et al. | 424/443 |
| 2008/0292879 | A1 | * | 11/2008 | Kumamoto et al. | 428/339 |
| 2009/0101867 | A1 | * | 4/2009 | Ishikawa et al. | 252/183.12 |

FOREIGN PATENT DOCUMENTS

| | | |
|---|---|---|
| CN | 1196671 A * | 10/1998 |
| EP | 0 427 475 | 5/1991 |
| EP | 0 786 240 A1 | 7/1997 |
| EP | 0 856 302 A1 | 8/1998 |
| JP | 60-106622 | 7/1985 |
| JP | 61-83400 | 4/1986 |
| JP | 1-201253 | 8/1989 |
| JP | 2572621 | 8/1989 |
| JP | 3-28301 | 2/1991 |
| JP | 4-185791 | 7/1992 |
| JP | 8-49188 | 2/1996 |
| JP | 8-112303 | 5/1996 |
| JP | 8-332197 | 12/1996 |
| JP | 10-212690 | 8/1998 |
| JP | 10-314208 | 12/1998 |
| JP | 11-353 | 1/1999 |
| JP | 11-181696 | 7/1999 |
| JP | 2000-212890 | 8/2000 |
| JP | 2000-262548 | 9/2000 |
| JP | 2000-294365 | 10/2000 |
| JP | 2001-198150 | 7/2001 |
| JP | 2003-102761 | 4/2003 |
| JP | 2004202198 A * | 7/2004 |
| JP | 2005224316 A * | 8/2005 |
| JP | 2005328852 A * | 12/2005 |
| JP | 2006314618 A * | 11/2006 |
| WO | WO 96/11654 | 4/1996 |
| WO | WO 02/36051 A1 | 5/2002 |
| WO | WO 2004041135 A1 * | 5/2004 |

OTHER PUBLICATIONS

Englisg Translation of JP Publication No. Hei-01-201253, Aug. 14, 1989.*
U.S. Appl. No. 10/556,136, filed Nov. 9, 2005, Kumamoto, et al.
U.S. Appl. No. 12/063,476, filed Feb. 11, 2008, Ishikawa, et al.
U.S. Appl. No. 10/566,471, filed Jan. 31, 2006, Kumamoto, et al.

* cited by examiner

*Primary Examiner*—José A Fortuna
(74) *Attorney, Agent, or Firm*—Oblon, Spivak, McClelland, Maier & Neustadt, L.L.P.

(57) ABSTRACT

A molded sheet containing at least an oxidizable metal, a moisture retaining agent, and a fibrous material and having a content of components other than the fibrous material of 50% by weight or higher. The sheet has a thickness of 0.08 to 1.2 mm and a breaking length of 100 to 4000 m.

19 Claims, 2 Drawing Sheets

MOLDED SHEET

TECHNICAL FIELD

The present invention relates to a heat generating sheet utilizing heat generation accompanying oxidation of an oxidizable metal with oxygen in air, particularly a heat generating sheet also usable as a steam generating sheet, a method of producing the same, and a molded sheet used for the production of the same.

BACKGROUND ART

The method disclosed in Japanese Patent 2572621 is among known techniques pertinent to production of a molded article that generates heat using oxidation reaction of oxidizable metal powder with oxygen in air.

According to the method, a raw material slurry is prepared by suspending a fibrous substance in water and adding thereto an oxidizable metal, e.g., iron powder, activated carbon as a moisture retaining agent, an electrolyte as a reaction promoter, etc. A wet web is prepared from the slurry by a papermaking process, dewatered by suction, and pressed into a heat generating molded article of sheet form having a water content of 5 to 65 wt %.

The heat generating molded article manufactured by the method is as thick as 0.2 to 10 mm. As the oxidation reaction proceeds, it becomes brittle and loses flexibility. Therefore, when applied as, for example, a warming sheet to a bending part of a body, such as an elbow or a knee, with that thickness, it becomes uncomfortable to wear with time. In applications to self-heating containers or keep-warm containers, the molded article has difficulty in closely conforming to some containers. The technique has additional disadvantages such that the molded article has poor fabricability in, e.g., trimming; that oxidation is liable to occur in the slurry by oxygen in the slurry and in air, which can cause reduction of performance and can rust equipment; and that the molded article cannot be taken up in roll, which has been a bar to productivity.

Accordingly, an object of the present invention is to provide a heat generating sheet excellent in not only conformability to a part of a body or a container but fabricability and productivity, a method of producing the heat generating sheet, a molded sheet used in the production of the heat generating sheet, and a method of producing the molded sheet.

DISCLOSURE OF THE INVENTION

As described above, the conventional heat generating sheet is prepared from a raw material slurry containing an oxidizable metal powder, a moisture retaining agent, and an electrolyte as a reaction promoter. Therefore, when the sheet fabricated of the slurry by papermaking is dried by heating oxidation of the oxidizable metal is accelerated, and the resulting heat generating sheet has reduced heat generating performance and reduced mechanical strength.

The present inventors have found that oxidation of an oxidizable metal during the production of a heat generating sheet can be suppressed by preparing a wet web by papermaking using an electrolyte-free raw material composition containing an oxidizable metal, a fibrous material, and water, positively heat-drying the wet web, and incorporating an electrolyte into the resulting molded sheet. They have ascertained that their technique achieves strength, fabricability, productivity, and storage stability.

The present invention is an accomplishment based on the above findings. The present invention provides a molded sheet containing at least an oxidizable metal, a moisture retaining agent, and a fibrous material. The content of components other than the fibrous material in the molded sheet is 50% by weight or higher. The molded sheet has a thickness of 0.08 to 1.2 mm and a breaking length of 100 to 4000 m.

The present invention also provides a heat generating sheet that is the molded sheet of the present invention impregnated with an electrolyte.

The present invention also provides a method of producing a molded sheet including the steps of forming a wet web by a papermaking process using a raw material composition containing at least an oxidizable metal, a moisture retaining agent, and a fibrous material, dewatering the wet web, and drying the wet web.

The present invention also provides a molded sheet produced by the method of producing a molded sheet according to the present invention.

The present invention also provides a method of producing a heat generating sheet including the step of impregnating a molded sheet with an electrolytic solution. The molded sheet is one produced by the method of producing a molded sheet according to the present invention.

The present invention also provides a heat generating sheet produced by the method of producing a heat generating sheet according to the present invention.

BEST MODE FOR CARRYING OUT THE INVENTION

Figure 1:
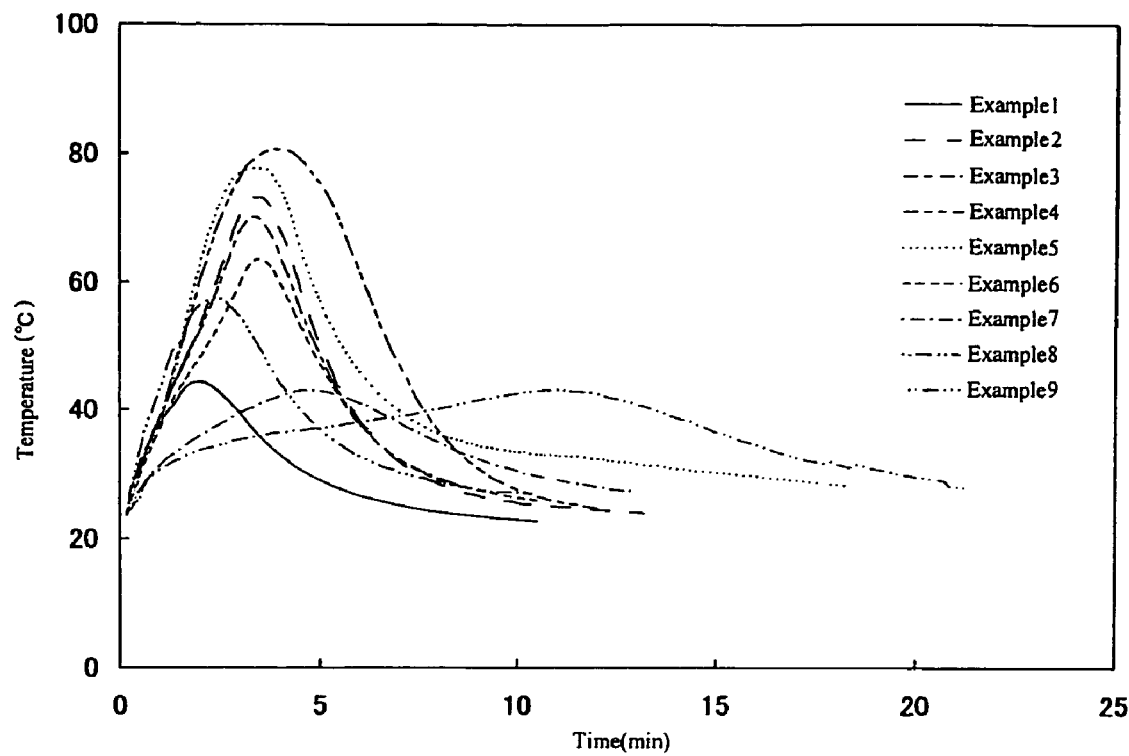
FIG. 1 is a graph representing the heat generation characteristics of the heat generating sheets obtained in Examples of the present invention.

The present invention will be described based on its preferred embodiments with reference to the accompanying drawings.

The molded sheet according to the present invention contains at least an oxidizable metal, a moisture retaining agent, and a fibrous material.

The molded sheet of the present invention contains at least 50% by weight, preferably 70% by weight or more, more preferably 80% by weight or more, of components other than the fibrous material. If the content of the components other than the fibrous material is less than 50% by weight, a heat generating sheet obtained therefrom can fail to heat up to or above the temperature felt hot by the finger. The higher the content of the components other than the fibrous material, the more preferred. Nevertheless, the upper limit is 98% by weight for assuring strength necessary to maintain fabricability of the molded sheet.

The oxidizable metal is not particularly limited, and any oxidizable metals commonly employed in this type of heat generating molded articles can be made use of. The oxidizable metal preferably has a particulate or fibrous form from the standpoint of handling and molding properties.

Particulate oxidizable metals include iron powder, aluminum powder, zinc powder, manganese powder, magnesium powder, and calcium powder. Iron powder is preferred of them because of its handling properties, safety, and production cost. The particulate oxidizable metal preferably has a particle size of 0.1 to 300 μm for fixability onto the fibrous material (described infra) and ease of reaction control. The term "particle size" as used herein means a maximum length of powder particles or an average particle size measured by a dynamic light scattering method, a laser diffraction method, and the like. It is more preferred to use powder containing those particles having a particle size of 0.1 to 150 μm in a proportion of 50% by weight or more.

Fibrous oxidizable metals include steel fiber, aluminum fiber, and magnesium fiber. Steel fiber, aluminum fiber, and the like are preferred for handling properties, safety, and production cost. The fibrous oxidizable metal preferably has a fiber length of 0.1 to 50 mm and a thickness of 1 to 1000 μm from the viewpoint of molding properties and the mechanical strength, surface smoothness and heat generating performance of the resulting sheet.

The proportion of the oxidizable metal in the molded sheet is preferably 10% to 95% by weight, more preferably 30% to 80% by weight. With less than 10% by weight of the oxidizable metal, a heat generating sheet obtained from the molded sheet can fail to heat up to or above the temperature felt hot to the touch of fingers, and the relatively increased proportions of the fibrous material and a binding component (e.g., a flocculant) hereinafter described can make the sheet harder and less comfortable to use. With a higher content than 95% by weight, there can arise the following problems. A heat generating sheet obtained from the molded sheet tends to undergo formation of an oxide film of the oxidizable metal, etc. on its surface. The oxide film impairs air permeability. It follows that the reaction hardly propagates into the inside of the heat generating sheet, resulting in a failure to reach a desired temperature. The oxidizable metal shows setting expansion on oxidation, which makes the sheet hard, shortens the duration of heat generation, hinders sufficient moisture supply by the moisture retaining agent, and causes fall-off of the oxidizable metal. The relatively decreased proportions of the fibrous material and binding component hereinafter described in the molded sheet can result in reduction of mechanical strength characteristics such as flexural strength and tensile strength. The oxidizable metal content in the molded sheet can be determined by ash content measurement in accordance with JIS P8128, vibrating sample magnetization measurement (applicable to iron, of which the magnetization on applying an external magnetic field is made use of), etc.

The moisture retaining agent includes any moisture retaining agents commonly employed in heat generating sheets with no particular limitation. The moisture retaining agent not only serves for moisture retention but functions as an agent for holding and supplying oxygen to the oxidizable metal. Useful moisture retaining agents include activated carbon (palm shell charcoal, wood charcoal, bituminous coal, peat, and lignite), carbon black, acetylene black, graphite, zeolite, pearlite, vermiculite, silica, cancrinite, and fluorite. Preferred of them is activated carbon for its moisture retaining ability, oxygen supplying ability, and catalytic ability. It is preferred to use a particulate moisture retaining agent having a particle size of 0.1 to 500 μm, particularly the one containing those particles with a particle size of 0.1 to 200 μm in a proportion of 50% by weight or more, in view of the capability of providing an effective contact with the oxidizable metal. Moisture retaining agents of other forms are also usable. For example, those of fibrous form such as activated carbon fiber can be used.

The moisture retaining agent is preferably present in the molded sheet in an amount of 0.5% to 60% by weight, more preferably 1% to 50% by weight. At a moisture retaining agent content lower than 0.5% by weight, the molded sheet may fail to hold a requisite water content for sustaining sufficient oxidation reaction for keeping the temperature above the body temperature. Besides, the air permeability of the sheet becomes insufficient for oxygen supply, tending to result in poor heat generation efficiency. Where the moisture retaining agent content exceeds 60% by weight, the following problems can result. A heat generating sheet obtained from the molded sheet has an increased heat capacity for the amount of heat generated only to show a small temperature rise, which may not be felt hot by the skin. The moisture retaining agent tends to fall off. Relative reduction in the proportions of the fibrous material and binding component hereinafter described can result in reduction of mechanical strength such as flexural strength and tensile strength.

The fibrous material includes natural fibers, and synthetic fibers. The natural fibers include plant fibers, such as cotton, kapok fiber, wood pulp, non-wood pulp, peanut protein fiber, corn protein fiber, soybean protein fiber, mannan fiber, rubber fiber, hemp, Manila fiber, sisal fiber, New Zealand flax, Luo Buma, coconut, rush, and straw; animal fibers, such as wool, goat hair, mohair, cashmere, alpaca, angora, camel, vicuna, silk, down, small feather, alginate fiber, chitin fiber, and casein fiber; and mineral fibers, such as asbestos. The synthetic fibers include semi-synthetic ones, such as cellulose diacetate, cellulose triacetate, oxidized acetate, promix, chlorinated rubber, and rubber hydrochloride; metal fibers; carbon fiber; and glass fiber. Also useful are single-component fibers made of polyolefin (e.g., high-density polyethylene, medium-density polyethylene, low-density polyethylene or polypropylene), polyester, polyvinylidene chloride, starch, polyvinyl alcohol or polyvinyl acetate, a copolymer thereof, or a modified product thereof; and core/sheath conjugate fibers having the above-recited resin component as a sheath. Of these fibers, polyolefin fibers and modified polyester fibers are preferably used for high bonding strength between individual fibers, high ability to form a three-dimensional network structure on fusion bonding of individual fibers, and lower melting point than the ignition point of pulp fiber. Synthetic fibers of polymers having branches, such as branched polyolefin fibers, are also preferred for securing good immobilization of the oxidizable metal and the moisture retaining agent. The above-recited fibrous materials can be used either individually or as a combination of two or more thereof. Recycled products of these fibrous materials are also employable. Among these fibrous materials particularly preferred are wood pulp and cotton in view of their immobilizing capabilities for the oxidizable metal and the moisture retaining agent, flexibility of the resulting molded sheet, oxygen permeability of the resulting sheet owing to the presence of interstitial voids, and the cost of production.

It is preferred for the fibrous material to have a CSF (Canadian Standard Freeness) of 600 ml or less, more preferably 450 ml or less. Fibrous materials having a CSF higher than 600 ml tend to have too poor ability to fix and hold such components as the oxidizable metal and the moisture retaining agent to hold prescribed amounts of the components, which results in poor heat generating performance and molding defects, such as unevenness of sheet thickness. The poor immobilizing ability of a high-freeness fibrous material will also cause fall-off of the components, insufficient entanglement between the fibrous material and the components, and reduction of bonding strength relying on hydrogen bonding. As a result, the sheet would have reduced mechanical strength such as flexural strength and tensile strength, and poor fabricability.

It is desirable for the fibrous material to have as low a CSF as possible. In general papermaking using pulp fiber as a sole fibrous material, when the proportion of components other than pulp fiber is small, a CSF less than 100 ml means very poor drainage making dewatering difficult. It can follow that the resulting molded sheet has thickness unevenness or suffers from molding defects such as burst of blisters on drying. According to the present invention, in contrast, the presence of the components other than the fibrous material in high proportions contributes to optimization of drainage and provides a molded sheet with a uniform thickness. A lower CSF indicates a higher fibril content, and a higher fibril content secures better immobilization of the components other than the fibrous material on the fibrous material, which results in high sheet strength.

The CSF of a fibrous material can be controlled by, for example, the degree of beating. The CSF is also adjustable by blending fibers different in CSF.

The fibrous material preferably has a negative zeta potential. "Zeta potential" is an apparent potential at the shear plane between a charged particle and a solution, which can be determined by streaming potential measurement or electrophoresis measurement. A fibrous material having a positive zeta potential has considerably reduced capability of immobilizing the above-mentioned components including the oxidizable metal and the moisture retaining agent and is liable to fail to maintain predetermined amounts of the components, resulting in poor heat generating performance. Increased amounts of these components would be lost with waste water, which can adversely affect the productivity and environmental conservation.

The fibrous material preferably has an average length of 0.1 to 50 mm, more preferably 0.2 to 20 mm. Too short fibers tend to fail to secure sufficient mechanical strength (such as flexural strength and tensile strength) of the molded sheet. Too short fibers will make too dense a fibrous layer, and too dense a molded sheet will have impaired air permeability, i.e., poor oxygen supply, resulting in insufficient heat generation. Too long fibers are difficult to disperse uniformly in a molded sheet, leading to a failure to obtain uniform mechanical strength or uniform sheet thickness. In addition, the increased fiber distance results in reduced capability of holding the oxidizable metal, the moisture retaining agent, and the like, easily allowing these components to fall off.

The fibrous material content in the molded sheet is preferably 2% to 50% by weight, more preferably 5 to 40% by weight. Where the content is less than 2% by weight, the effect for preventing the oxidizable metal and the moisture retaining agent from falling off is reduced, and the molded sheet tends to be very brittle. If the fibrous material content is more than 50% by weight, a heat generating molded article will have an increased heat capacity for the amount of heat generated, and a reduced rise in temperature results. Furthermore, the proportion of the other components including the oxidizable metal and the moisture retaining agent is so low that the resulting molding sheet can fail to exhibit desired heat generating performance.

A flocculant may be incorporated into the molded sheet as described infra.

If desired, the molded sheet may contain additives commonly used in papermaking, such as sizes, colorants, strengthening agents, yield improvers, loading materials, thickeners, pH control agents, and bulking agents, with no particular limitation. The amounts of the additives to be added can be selected appropriately according to the kinds.

The thickness of the molded sheet is 0.08 to 1.2 mm, preferably 0.1 to 0.6 mm. A molded sheet with a thickness smaller than 0.08 mm is liable to have insufficient heat generating performance, insufficient mechanical strength, and poor immobilizing capability for the components such as the oxidizable metal and the moisture retaining agent. Such a thin sheet is difficult to form with uniform thickness and composition in a stable manner and easily breaks due to pinhole development and the like, resulting in poor productivity and fabricability. A sheet with a thickness greater than 1.2 mm has a drastically reduced bending strength and easily undergoes brittle fracture. Such a thick sheet is likely to be too hard to provide a good fit only to cause discomfort particularly when applied as a warming sheet to a bending part of a body, such as an elbow, a knee, and the face. In addition, a thick sheet needs a long time for wet web formation and drying, which can result in not only poor productivity but reduction in heat generating performance or poor fabricability (i.e., liability to breakage of fracture).

The basis weight of the molded sheet is preferably 10 to 1000 $g/m^2$, more preferably 50 to 600 $g/m^2$. When, for example, an oxidizable metal having a high specific gravity is used, it tends to be difficult to stably form a sheet having a basis weight less than 10 $g/m^2$. A sheet with a basis weight greater than 1000 $g/m^2$ tends to feel so heavy as to give discomfort to a user or have deteriorated productivity or workability.

The molded sheet has a breaking length of 100 to 4000 m, preferably 200 to 3000 m. Where the breaking length is shorter than 100 m, it is difficult to form the sheet in a stable manner without breaks or tears; the resulting sheet is difficult to fabricate due to liability to breaking or tearing; and the final product is apt to lack in elasticity, crumble easily, and give discomfort to a wearer. A molded sheet with a breaking length exceeding 4000 m, which should contain large amounts of the fibrous material and the binding component making up the molded sheet, tends to be hard and rigid and to have poor heat generating performance.

A preferred embodiment of the heat generating sheet according to the present invention will then be described.

The heat generating sheet of the present invention is the above-described molded sheet of the present invention having been impregnated with a solution of an electrolyte, namely, an electrolytic solution.

The electrolyte to be added is not particularly limited, and any kind commonly used in this type of heat generating sheets can be used. Examples of useful electrolytes include sulfates, carbonates, chlorides and hydroxides of alkali metals, alkaline earth metals or heavy metals. Preferred of them are chlorides, such as sodium chloride, potassium chloride, calcium chloride, magnesium chloride, and iron (I) or (II) chloride, in view of their electrical conductivity, chemical stability, and production cost. These electrolytes can be used either individually or as a combination of two or more thereof.

The electrolyte is preferably added in an amount of 0.5% to 30% by weight, more preferably 1% to 25% by weight, based on the water content of the resulting heat generating sheet. Where the amount of the electrolyte is less than 0.5% by weight of the water content, the oxidation reaction of the resulting heat generating sheet may be suppressed, and the water content must by increased so as to secure a requisite amount of the electrolyte for heat generation. As a result, the heat capacity of the heat generating sheet increases, which can result in a reduction of the temperature rise. If the amount of the electrolyte exceeds 30% by weight of the water content, excess of the electrolyte may precipitate to impair air permeability of the resulting heat generating sheet. Furthermore, the water content in the heat generating sheet, with which a sufficient amount of the electrolyte for heat generation is secured, tends to be too small to supply a sufficient amount of water to the oxidizable metal, etc., and, as a result, the heat generating sheet exhibits poor heat generating performance. Moreover, uniform distribution of the electrolyte throughout the heat generating sheet tends to be difficult.

The water content of the heat generating sheet is preferably 10% to 80%, more preferably 20% to 60% (on a weight basis; hereinafter the same). A water content less than 10% tends to be insufficient for sustaining oxidation reaction. The reaction can come to the end halfway. Besides, it is difficult to distribute such a small amount of water uniformly throughout the heat generating sheet, tending to result in a failure to assure uniform heat generation. With a water content more than 80%, the heat generating sheet will have an increased heat capacity for the amount of heat generated, which can result in reduction of temperature rise. In addition, the air permeability of the heat generating sheet is impaired, resulting in poor heat generating performance. The sheet may have reduced shape retention and mechanical strength. The increased heat capacity of the heat generating sheet can result in a failure to raise the temperature of heat generation.

The temperature reachable by heat generation of the heat generating sheet of the present invention can arbitrarily be set by the formulation of the aforementioned components depending on the usage of the final product, that is, whether a steep temperature rise is desired or whether a long duration of heat generating reaction at a relatively low temperature is desired, and the like. The highest temperature reached by heat generation of the heat generating sheet of the present invention in terms of, for example, the temperature measured by the method adopted in Examples given later is preferably 30° to 100° C., more preferably 35° to 90° C.

Similarly to the highest temperature reachable, the amount of water vapor (steam) generated from the heat generating sheet of the present invention can arbitrarily be set by the formulation of the aforementioned components depending on the usage of the final product, that is, whether a steep temperature rise is desired or whether a long duration of heat generating reaction at a relatively low temperature is desired, and the like. The amount of water vapor generated from the heat generating sheet of the present invention is preferably 50 to 1000 mg, more preferably 100 to 600 mg, as measured by the method adopted in Examples given infra.

Method of producing the heat generating sheet according to the present invention will be described hereunder based on its preferred embodiments.

Method of producing of the heat generating sheet starts with preparation of a raw material composition (slurry) containing at least the oxidizable metal, the moisture retaining agent, the fibrous material, and water.

A flocculant is preferably added to the raw material composition as referred to above.

Examples of the flocculant include inorganic ones, such as metal salts, e.g., ammonium sulfate, polyaluminum chloride, ferric chloride, polyferric sulfate, and ferrous sulfate; polymeric ones, such as polyacrylamides, sodium polyacrylates, Mannich base-modified polyacrylamide, aminoalkyl poly (meth)acrylates, sodium carboxymethyl celluloses, chitosans, starches, and polyamide-epichlorohydrins; organic flocculants, such as dimethyldiallylammonium chloride type or ethyleneimine type alkylene dichloride-polyalkylenepolyamine condensates and dicyandiamide-formalin condensates; clay minerals, such as montmorillonite and bentonite; silicon dioxide and its hydrates, such as colloidal silica; and hydrous magnesium silicate, such as talc. Preferred of these flocculants are combinations of an anionic agent and a cationic agent from the standpoint of sheet surface properties, formation, molding properties, immobilizing properties for the above-described components such as the oxidizable metal and the moisture retaining agent, and sheet strength. Suitable combinations include a combination of anionic colloidal silica or bentonite and cationic starch or polyacrylamide and a combination of anionic sodium carboxymethyl cellulose and a cationic polyamide-epichlorohydrin resin. In addition to these combinations, the above-recited flocculants can be used either individually or in combination of two or more thereof.

The flocculant is preferably added in an amount of 0.01% to 5% by weight, more preferably 0.05% to 1% by weight, based on the solids content of the raw material composition. Less than 0.01% by weight of the flocculant has so poor flocculating effect that the above-described components such as the oxidizable metal and the moisture retaining agent tend to fall off in the papermaking step and that the raw material composition tends to be non-uniform only to provide a sheet with a non-uniform thickness and composition. More than 5% by weight of the flocculant tends to stick to drying rolls in the step of sheet drying or become a main cause of breaking or scorching, resulting in reduction of productivity. Too much flocculant also tends to destroy the potential balance of the raw material composition, which can result in increased fall-off of the components into white water during the step of papermaking. Moreover, oxidation may proceed in the molded sheet, resulting in reduction of storage stability of heat generating performance and strength.

The concentration of the raw material composition preferably ranges 0.05% to 10% by weight, more preferably 0.1% to 2% by weight. Concentrations lower than 0.05% require not only a large quantity of water but much time for wet web formation, tending to make it difficult to form a sheet with a uniform thickness. Concentrations higher than 10% easily cause insufficient dispersion of components only to provide a sheet with poor surface properties or a non-uniform thickness.

The raw material composition is made into a web by a papermaking process to obtain the above-described molded sheet.

Papermaking processes used to form a web include continuous papermaking by use of a cylinder paper machine, a foundrinier paper machine, a short-wire paper machine, a twin-wire paper machine, etc.; and batch papermaking such as manual papermaking. A molded sheet having a multilayer structure may be made by successively using raw material compositions of different formulations. A multilayered molded sheet may also be obtained by laminating sheets separately prepared from raw material compositions having different formulations.

The thus formed wet web is dewatered preferably to a water content (on a weight basis; hereinafter the same) of 70% or less, more preferably 60% or less, for assuring shape retention and mechanical strength. Dewatering is carried out by, for example, suction, application of pressurized air or pressing with a pressure roll or a pressure plate.

In the present invention, the sheet containing the oxidizable metal (having a property of reacting on being heated in an ordinary atmosphere) is then subjected to positive drying to remove the water content thereby providing a molded sheet which is inhibited from inducing oxidation of the oxidizable metal during the subsequent fabrication steps and has excellent long-term storage stability. Drying of the sheet is preferably carried out after wet web formation and before addition of the aforementioned electrolytic solution so that the oxidizable metal may be firmly fixed and held by the fibrous material and be prevented from falling off and that mechanical strength improvement by addition of a heat fusible component or a thermal crosslinking component may be expected.

The molded sheet is preferably dried by heating. The heating temperature is preferably 60° to 300° C., more preferably 80° to 250° C. If the heat drying temperature is too low, the drying time must be extended, and removal of water may accompany acceleration of oxidation of the oxidizable metal, which can result in reduction of heat generating performance of the heat generating sheet. Accelerated oxidation of the oxidizable metal is apt to occur in only the skin on both sides of the sheet to cause color change to pale brown. Too high a drying temperature invites not only deterioration in performance of the moisture retaining agent, etc., which results in reduction of heat generating performance of the heat generating sheet, but also abrupt water vaporization inside the sheet, which can destroy the sheet structure.

The drying is preferably effected to reduce the water content of the molded sheet to 20% or less, more preferably 10% or less. Where the water content exceeds 20%, the sheet has poor long-term storage stability. For example, when the sheet is temporarily stored in a roll form, excess of water is apt to migrate in the radial direction of the roll, resulting in variations of heat generating performance and mechanical strength.

The method of drying is selected appropriately depending on the sheet thickness, the treatment given to the sheet before drying, the water contents before and after the drying, and the like. Useful drying methods include contact with a heating structure (heat generating element), application of heated air or steam (superheated steam), vacuum drying, microwave heating, and ohmic heating. The drying may be carried out simultaneously with the above-described dewatering.

The shaping of the wet web by dewatering and drying is preferably conducted in an inert gas atmosphere. Because the web to be shaped is free from an electrolyte that acts as an oxidation promoter, the shaping may be performed in an ordinary air atmosphere if desired, which enables simplification of equipment. Where necessary, the sheet can be fabricated by craping, slitting, trimming or any other methods for shaping or forming. Thin and yet tearproof, the resulting molded sheet can be taken up in a roll. A plurality of the sheets may be stacked one on another, or the sheet or a plurality of the sheet may be laminated with another film or sheet (e.g., paper, woven fabric, nonwoven fabric or plastic film), and the stack or the laminate may be pressed into a unitary sheet or be embossed or needle punched to provide a sheet or a laminate sheet with an uneven pattern or perforations. A thermoplastic resin component or a hot-water-soluble component may be incorporated into the raw material composition to make sheets ready to be joined to each other by heat sealing.

The electrolyte is then incorporated into the molded sheet. This step is preferably carried out in an inert gas atmosphere such as nitrogen or argon. Where the electrolyte is incorporated by impregnation with an electrolytic solution, the impregnating step may be conducted in an ordinary air atmosphere because oxidation that may proceed immediately after impregnation is mild. The electrolyte to be incorporated is the same as used in the aforementioned heat generating sheet.

The method for incorporating the electrolyte into the sheet is selected appropriately according to the treatment given to the sheet after papermaking, the water content and the form of the sheet, and the like. For example, the electrolyte can be incorporated by impregnating the molded sheet with an electrolytic solution having a prescribed electrolyte concentration or adding a powdered electrolyte having a prescribed particle size directly to the sheet. Impregnation is preferred for achieving uniform distribution of the electrolyte and simultaneously controlling the water content of the resulting sheet.

Where the electrolyte is incorporated by impregnating the molded sheet with an electrolytic solution as described above, the manner of impregnation is chosen according to the form (e.g., thickness) and the water content of the sheet. Impregnation methods include spraying, syringing into part of the sheet (the injected electrolytic solution penetrates throughout the sheet by capillarity), coating with a brush, etc., soaking in the electrolytic solution, gravure coating, reverse coating, doctor blade coating, and so forth. Spraying is preferred for uniform distribution, ease of operation, and relatively low cost of equipment. In manufacturing commodities having a complicated shape or layer structure, syringing is preferred for productivity, method flexibility (the final finishing method can be done in a separate step), and simplicity of equipment. It is possible to conduct syringing after the molded sheet is enclosed in an oxygen barrier holder, etc.

If necessary, the water content of the molded sheet containing the electrolyte is adjusted to stabilize the heat generating sheet. The heat generating sheet thus prepared can be fabricated by trimming to size, or two or more of the heat generating sheets are superposed on each other to a prescribed thickness.

The surface of the resulting heat generating sheet is given a cover layer having oxygen permeability. The cover layer has oxygen permeability over the entire area thereof or in part thereof. The cover layer may be of any material having oxygen permeability. The cover layer is provided by superposing paper, nonwoven fabric, a microporous film, a finely perforated resin film, etc. on the heat generating sheet or by coating or impregnating the heat generating sheet with a synthetic resin coating, an emulsion coating, etc.

The heat/steam generation characteristics of the heat generating sheet can be controlled freely by the oxygen permeability of the cover layer. Indications of oxygen permeability include water vapor transmission rate, i.e., moisture permeability. Choosing a cover layer having high moisture permeability provides a heat generating sheet that can reach a high temperature in a short time to exhibit high steam generation characteristics. Choosing a cover layer with low moisture permeability provides a heat generating sheet that exhibits mild heat and steam generation characteristics for an extended period of time.

The heat generating sheet is supplied to the market in oxygen impermeable and moisture impermeable packages so as to be kept away from oxygen until use.

As described above, the molded sheet of the invention and the heat generating sheet prepared therefrom are thin, tearproof, and flexible and therefore excellent in conformability to a part of a body or a container, fabricability, and productivity.

The raw material composition (suspension), being free from an electrolyte serving as an oxidation promoter, has a reduced ion concentration and therefore shows satisfactory dispersing capability for the oxidizable metal powder. By bringing the oxidizable metal and the fibrous material into substantial contact in the preparation of the raw material composition, the oxidizable metal is uniformly fixed on the surface of the fibrous material to provide a heat generating molded article with improved heat generation characteristics.

A suspension having incorporated therein an electrolyte acting as an oxidation promoter has an increased salt concentration so that the electrical double layer in the interface on the aforementioned components including the oxidizable metal and the moisture retaining agent and on the fibrous material is compressed. As a result, the contact between the components and the fibrous material is considerably inhibited, making immobilization of the components onto the fibrous material difficult. This being the case, it is difficult to mold a sheet that is thin and yet loaded with a large amount of the components. Immobilization with the aid of a flocculant is also difficult in such a high salt concentration system for the same reason. Thus, the resulting heat generating sheet would have markedly inferior heat generation characteristics. Furthermore, reaction with oxygen in water can occur to provoke oxidation reaction, resulting in reduction of heat generating performance. In addition, the molded sheet easily reacts with oxygen in air, which can cause reduction of long-term storage stability or can rust molding and fabricating equipment such as a papermaking machine.

It is the electrolyte-free molded sheet that is previously dried and shape. This brings about the following advantages. The molded sheet maintains its strength and easy to fabricate. A cutting blade is protected from rust and wear. In the step of impregnation, it is easy to control the amounts of the electrolyte and water to be present in the heat generating sheet. It is possible to make a heat generating sheet having a part capable of heat generation and a part incapable of heat generation on the same plane by conducting the impregnation in an arbitrary pattern. Because oxidation of the oxidizable metal during the production steps can be minimized, heat generating molded products with satisfactory heat generation characteristics can be obtained.

The present invention is not deemed to be limited to the foregoing embodiments and is subject to appropriate changes and modifications without departing from the spirit and scope thereof.

The heat generating sheet of the present invention is not only applicable as an ultrathin body warmer as such but can be combined with various functional agents to exert various functions in addition to the heat generating function and the steam generating function for a variety of applications. For example, functions of cleaning and disinfection, slow wax release, perfuming, deodorization, and the like may be added to offer hot sheets for home care applications, such as cleaning wood floors, tatami mats, stoves, and ventilation fans; air care applications for making the air comfortable; car care applications, such as cleaning and waxing; face, body, hand or foot skin care applications, such as cleaning, disinfection, moisturization, sebum removal, and reduction of wrinkles, dark circles (in eye area), and dullness; and health care applications for soothing pain or cramps during menstruation by wrapping around or sticking to the neck, shoulder, hip, hand, leg, etc.

The heat generating sheet may be combined with a facial pack to provide a hot pack that can be used for skin care applications for moisturization or reduction of dark circles in eye area, wrinkles or dullness or for eye care applications for recovering eyesight. It may be combined with cataplasm to provide a hot cataplasm that can be applied to the neck, shoulder, leg, hip, etc. for soothing pain or cramps. It may be combined with a hair cap to provide a warming hair cap that can be used in permanent waving, hair dyeing, hair growth promotion or a like hair care application. The heat generating sheet may be shaped to a mitten for hand care applications or to a sock for foot care applications. The heat generating sheet may be shaped with projections and depressions for use as a hot brush, etc.

The heat generating sheet is also applicable in the field of construction for removing harmful substances such as formalin (bake-out); in the field of adhesives for accelerating curing by heating; keep-warm or self-heating applications including food packaging and distribution resources; for use as emergency wearables, such as instant-heat clothes and blankets; and medical applications such as warming bandage. Furthermore, the oxidation reaction being taken advantage of, the heat generating sheet of the present invention is applicable as an antioxidant in various other applications for keep-fresh food packaging, anti-corrosion of metal, and prevention or protection from mold and moth in bedclothes, clothes, art works, etc.

Molded sheets having the formulation shown in Table 1 below (expressed in terms of weight percentage based on the solids content of the slurry) were prepared in Examples 1 to 9 and Comparative Examples 1 to 5. The resulting molded sheets were examined for thickness, basis weight, breaking length, and flexural strength. A heat generating sheet was prepared from each of the molded sheets as described below and was evaluated for heat generation characteristics (i.e., highest reachable temperature and during of heat generation) and steam generation characteristics. The results obtained are shown in Tables 2 and 3.

TABLE 1

|         |   | Formulation (wt %) |                    |                             | Formulation (parts by weight) |             |             | Immobilizing Ratio (%) | Content of Components Other than Fibrous Material (wt %) |
|---------|---|--------------------|--------------------|-----------------------------|-------------------------------|-------------|-------------|------------------------|----------------------------------------------------------|
|         |   | Oxidizable Metal   | Fibrous Material   | Moisture Retaining Agent    | Flocculant (parts)            | Electrolyte | CSF (ml)    |                        |                                                          |
| Example | 1 | 75                 | 10                 | 15                          | 0.75                          | 0           | 300         | *                      | *                                                        |
|         | 2 | 75                 | 10                 | 15                          | 0.75                          | 0           | 20          | 94                     | 89                                                       |
|         | 3 | 75                 | 10                 | 15                          | 0.75                          | 0           | 150         | 83                     | 88                                                       |
|         | 4 | 75                 | 10                 | 15                          | 0.75                          | 0           | 150         | 87                     | 89                                                       |
|         | 5 | 75                 | 10                 | 15                          | 0.75                          | 0           | 300         | *                      | *                                                        |
|         | 6 | 75                 | 10                 | 15                          | 0.75                          | 0           | 460         | 69                     | 85                                                       |
|         | 7 | 58                 | 30                 | 12                          | 0.75                          | 0           | 300         | *                      | *                                                        |
|         | 8 | 58                 | 30                 | 12                          | 0.75                          | 0           | 150         | 94                     | 68                                                       |
|         | 9 | 75                 | 10                 | 15                          | 0.75                          | 0           | 300         | *                      | *                                                        |
| Compara. Example | 1 | 75        | 10                 | 15                          | 0.75                          | 0           | 150         | 89                     | 89                                                       |
|         | 2 | 75                 | 10                 | 15                          | 0.75                          | 0           | 150         | **                     | **                                                       |
|         | 3 | 75                 | 10                 | 15                          | 0.75                          | 0           | 720         | 46                     | 78                                                       |
|         | 4 | 75                 | 10                 | 15                          | 0.75                          | 3           | 720         | 32                     | 69                                                       |
|         | 5 | 33                 | 60                 | 7                           | 0.75                          | 0           | 460         | 96                     | 38                                                       |

* Unmeasurable because molding was carried out by continuous papermaking using a papermaking machine.
** Unmeasurable due to a failure to mold into a sheet.

EXAMPLE 1

1) Formulation of Raw Material Composition

| | |
|---|---|
| Oxidizable metal: | |
| iron powder (under 45 μm mesh) RKH (trade name) produced by Dowa Iron Powder Co., Ltd. | 150 g |
| Fibrous material: | |
| Pulp fiber (NBKP) Skeena (trade name) produced by Skeena; average fiber length: 2.1 mm | 20 g |
| Polyvinyl alcohol fiber VPB107-1 (trade name) produced from Kuraray Co., Ltd. | 2.0 g |
| Moisture retaining agent: | |
| Activated carbon (under 45 μm mesh) Carboraffin (trade name) available from Takeda Chemical Industries, Ltd. | 30 g |
| Flocculant: | |
| Sodium carboxymethyl cellulose Cellogen WS-C (trade name) produced by Dai-ichi Kogyo Seiyaku Co., Ltd. | 0.5 g |
| Polyamide-epichlorohydrin resin WS547 (trade name) produced by Japan PMC Corp. | 0.5 g |
| Water: Industrial water | 99800 g |

2) Papermaking Conditions

A wet web was formed using the raw material composition by papermaking by means of a small-sized, tilted short-wire paper machine (possessed by Kochi Prefectural Paper Technology Center) at a line speed of 7 m/min.

3) Dewatering and Drying Conditions

The wet web was sandwiched and pressed between two felt pieces for dewatering and then passed as such through a pair of rolls heated to 120° C. at a line speed of 7 m/min for drying to a water content of 5% by weight or lower.

4) Measurement of Immobilizing Ratio

The immobilizing ratio of the resulting molded sheet was calculated from the solids weight of the raw material mixture used to form the molded sheet and the weight of the resulting molded sheet according to the following equation.

Immobilization ratio (%)=(weight of molded sheet× 100)/solids weight of raw material mixture

5) Measurement of Components Other than Fibrous Material

The content of the components other than the fibrous material in the resulting molded sheet was obtained from the composition and the solids weight of the raw material mixture and the dry weight of the molded sheet according to the following equation.

$b = Mh/Ms \times (100-a)$ where
Ms: solids weight of raw material composition
a: fibrous material content(%) in raw material mixture on a solid basis
Mh: dry weight of molded sheet
b: content (%) of components other than fibrous material in molded sheet.

6) Shape of Molded Sheet

As shown in Table 2, the sheets had a thickness ranging from 0.05 to 1.6 mm and a basis weight ranging from 40 to 1277 g/cm². The thickness was obtained as an average of measurements on at least five measuring points of the sheet in accordance with JIS P8118. The basis weight was calculated by dividing the weight of a sheet with an area of at least 100 cm² by the area of the sheet.

7) Measurement of Breaking Length

A 15 mm wide and 150 mm long test piece cut out of the molded sheet was set on a tensile tester at an initial gauge length of 100 mm and pulled at a pulling speed of 20 mm/min in accordance with JIS P8113. The breaking length was calculated according to equation:

Breaking length (m)=(1/9.8)×[(tensile strength (N/m)]×10⁶/[basis weight of test piece (g/m²)]

8) Measurement of Flexural Strength

A 15 mm wide and 150 mm long test piece cut out of the molded sheet was folded into half along the center of the length repeatedly and alternately in two opposite directions. The number of flexes until the molded sheet was broken was recorded.

9) Preparation of Heat Generating Sheet

Two resulting molded sheets (thickness: 0.14 mm each) were superposed on each other, and an electrolytic solution shown below was sprayed on the set of molded sheets to obtain a two-ply heat generating sheet having a water content of 36%.

Electrolytic solution:
Electrolyte: purified salt (NaCl)
Water: industrial water
Concentration: 3 wt %

10) Temperature Characterization of Heat Generating Sheet

A 50 mm square test piece cut out of the two-ply heat generating sheet was sandwiched between a moisture permeable sheet having a water vapor transmission rate of 5000 g/m²·24 hr (as measured in accordance with JIS Z0208) and a moisture impermeable sheet, and the moisture permeable sheet and the moisture impermeable sheet were sealed into a bag to prepare a sample. The sample was placed with its moisture permeable sheet side up and let to generate heat in a 4.2-liter closed chamber having a relative humidity of 1% or less and designed to be fed with 2.1 l/min of dry air. The temperature of the lower side of the sample measured with a thermocouple was taken as the heat generation temperature of the heat generating sheet.

11) Measurement of Steam Generated

The humidity of the air discharged from the above-described closed system was measured with a hygrometer, from which the amount of steam generated per unit time after the start of heat generation was calculated using equation (1) shown below. The cumulative amount of steam generated for a 10 minute period was taken as the "amount of steam generated". In formulae below, e represents a water vapor pressure (Pa); es represents a saturated water vapor pressure (Pa, quoted from JIS Z8806); T represents temperature (° C., dry bulb temperature); and s represents a sampling frequency (sec).

Relative humidity $U$ (% $RH$)=($e/es$)×100

Absolute humidity $D$ (g/m³)=(0.794×10⁻²×$e$)/(1+ 0.00366$T$)=(0.794×10⁻²×$U$×$es$)/[100×(1+ 0.00366$T$)]

Unit air volume $P(l)$=(2.1×$s$)/60

Amount of steam per unit time $A(g)$=($P$×$D$)/1000 (l)

EXAMPLE 2

A heat generating sheet was prepared in the same manner as in Example 1 with the following exceptions. The formulation of the raw material composition was altered as described below. The pulp fiber had a CSF of 20 ml. The above-described papermaking machine was replaced with a handsheet machine (according to JIS P8209; diameter: 170 mm) fitted with an 80 mesh wire manufactured by Kumagai Riki Kogyo K.K. The composition was agitated at 300 rpm for 1 minute to fix the components such as the oxidizable metal and the moisture retaining agent to the fiber. The wet web was dewatered and dried by pressing on a press under a pressure of 2 MPa for 3 minutes to reduce the water content to 1% by weight or lower. The thickness of the molded sheet was as shown in Table 2.

Formulation of Raw Material Composition:

| | |
|---|---|
| Oxidizable metal: | |
| iron powder (under 45 μm mesh) RKH (trade name) produced by Dowa Iron Powder Co., Ltd. | 7.5 g |
| Fibrous material: | |
| Pulp fiber (NBKP) Skeena (trade name) produced by Skeena | 1.0 g |
| Moisture retaining agent: | |
| Activated carbon (under 45 μm mesh) Carboraffin (trade name) available from Takeda Chemical Industries, Ltd. | 1.5 g |
| Flocculant: | |
| Sodium carboxymethyl cellulose Cellogen WS-C (trade name) produced by Dai-ichi Kogyo Seiyaku Co., Ltd. | 0.025 g |
| Polyamide-epichlorohydrin resin WS547 (trade name) produced by Japan PMC Corp. | 0.05 g |
| Water: Industrial water | 1490 g |

EXAMPLE 3

A heat generating sheet was prepared in the same manner as in Example 2, except for changing the CSF of the pulp fiber to 150 ml.

EXAMPLE 4

A heat generating sheet was prepared in the same manner as in Example 3, except that the amount of the raw material composition was doubled.

EXAMPLE 5

A heat generating sheet was prepared in the same manner as in Example 1, except that five molded sheets were stacked before impregnation of the electrolytic solution.

EXAMPLE 6

A heat generating sheet was prepared in the same manner as in Example 2, except for changing the CSF of the pulp fiber to 460 ml.

EXAMPLE 7

A heat generating sheet was prepared in the same manner as in Example 1, except that the amounts of the iron powder, pulp fiber, and activated carbon of the raw material composition were changed to 116 g, 60 g, and 24 g, respectively.

EXAMPLE 8

A heat generating sheet was prepared in the same manner as in Example 2, except that the amounts of the iron powder, pulp fiber, and activated carbon of the raw material composition were changed to 5.8 g, 3.0 g, and 1.2 g, respectively.

EXAMPLE 9

A heat generating sheet was prepared in the same manner as in Example 1, except for changing the amount of the PVA fiber of the fibrous material to 0.25 g.

COMPARATIVE EXAMPLES 1 AND 2

A heat generating sheet was prepared in the same manner as in Example 2, except for changing the thickness of the molded sheet form 1.60 mm (Comparative Example 1) and 0.5 mm (Comparative Example 2).

COMPARATIVE EXAMPLE 3

A heat generating sheet was prepared in the same manner as in Example 2, except for changing the CSF of the pulp fiber to 720 ml.

COMPARATIVE EXAMPLE 4

A heat generating sheet was prepared in the same manner as in Example 2, except for adding NaCl to the raw material composition in an amount of 3% by weight based on the raw material composition.

COMPARATIVE EXAMPLE 5

A heat generating sheet was prepared in the same manner as in Example 2, except that the amounts of the iron powder, pulp fiber, and activated carbon of the raw material composition were changed to 3.3 g, 6.0 g, and 0.7 g, respectively.

TABLE 2

| | | | Molded Sheet | | | | | |
|---|---|---|---|---|---|---|---|---|
| | | Molding Method | Thickness (mm) | Basis weight (g/m$^2$) | Breaking Length (m) | Number of Flexes | Angle at Break(°) | Molding Properties* |
| Example | 1 | papermaking machine | 0.14 | 110 | 780 | ≧200 | 90 | A |
| | 2 | handsheet machine | 0.62 | 464 | 342 | ≧200 | 90 | A |
| | 3 | handsheet machine | 0.52 | 388 | 280 | ≧200 | 90 | A |
| | 4 | handsheet machine | 1.02 | 822 | 317 | 5-100 | 80 | A |

TABLE 2-continued

|  |  | Molding Method | Molded Sheet | | | | | |
|---|---|---|---|---|---|---|---|---|
|  |  |  | Thickness (mm) | Basis weight (g/m$^2$) | Breaking Length (m) | Number of Flexes | Angle at Break(°) | Molding Properties* |
|  | 5 | papermaking machine | 0.14 | 120 | 780 | ≧200 | 90 | A |
|  | 6 | handsheet machine | 0.46 | 327 | 239 | ≧200 | 90 | A |
|  | 7 | handsheet machine | 0.17 | 112 | 1214 | ≧200 | 90 | A |
|  | 8 | handsheet machine | 0.62 | 433 | 1555 | ≧200 | 90 | A |
|  | 9 | papermaking machine | 0.18 | 133 | 147 | ≧200 | 90 | A |
| Compara. Example | 1 | handsheet machine | 1.60 | 1277 | 257 | 2 | 40 | B |
|  | 2 | handsheet machine | 0.05 | 40 | unmeasurable | unmeasurable | unmeasurable | C1 |
|  | 3 | handsheet machine | 0.38 | 247 | 126 | ≧200 | 90 | C2 |
|  | 4 | handsheet machine | 0.35 | 153 | 144 | ≧200 | 90 | C2 |
|  | 5 | handsheet machine | 0.66 | 468.0 | 4179 | ≧200 | 90 | A |

*A: good
B: Much time is needed for dewatering and drying because of large thickness.
C1: Failure to form pin hole-free sheet with uniform thickness.
C2: Large material loss due to poor fixability for powder, etc.

TABLE 3

|  |  | Heat Generating Sheet | | | |
|---|---|---|---|---|---|
|  |  | Number of Stacked Molded Sheets | Highest Reachable Temp. (°C.) | Duration of Maintaining at ≧40° C. (min)** | Amount of Generated Steam (mg) |
| Example | 1 | 2 | 44 | 1.5 | 102 |
|  | 2 | 1 | 73 | 4.5 | 344 |
|  | 3 | 1 | 70 | 4.5 | 282 |
|  | 4 | 1 | 81 | 6.3 | 681 |
|  | 5 | 5 | 78 | 5.7 | 364 |
|  | 6 | 1 | 64 | 4.3 | 225 |
|  | 7 | 2 | 43 | 3.1 | 149 |
|  | 8 | 1 | 43 | 5.3 | 137 |
|  | 9 | 3 | 59 | 3.7 | 187 |
| Compara. Example | 1 | 1 | 79 | 9.8 | 806 |
|  | 2 | 1 | unmeasurable | unmeasurable | unmeasurable |
|  | 3 | 1 | 41 | 0.5 | 106 |
|  | 4 | 1 | 28 | 0.0 | 58 |
|  | 5 | 1 | 26 | 0.0 | 64 |

**The time period in which heat generation to 40° C. or higher was sustained

Figure 2:
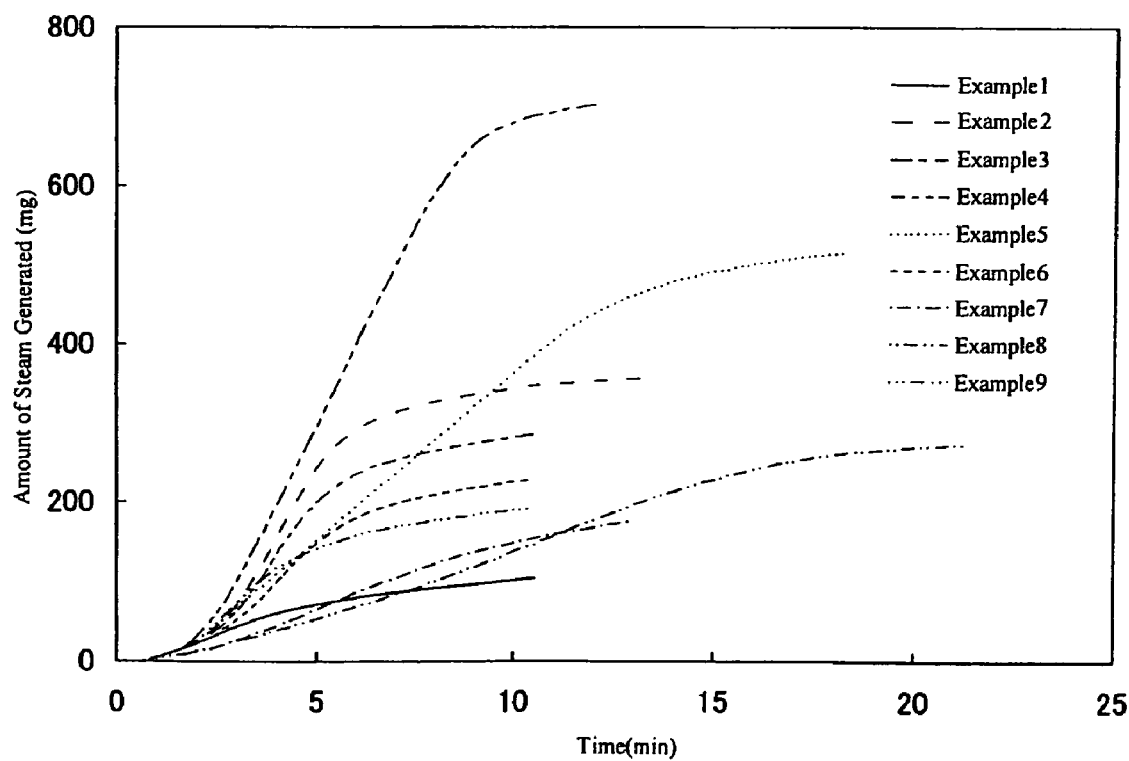
FIG. 2 is a graph showing the steam generation characteristics of the heat generating sheets obtained in Examples of the present invention.
Figure 3:
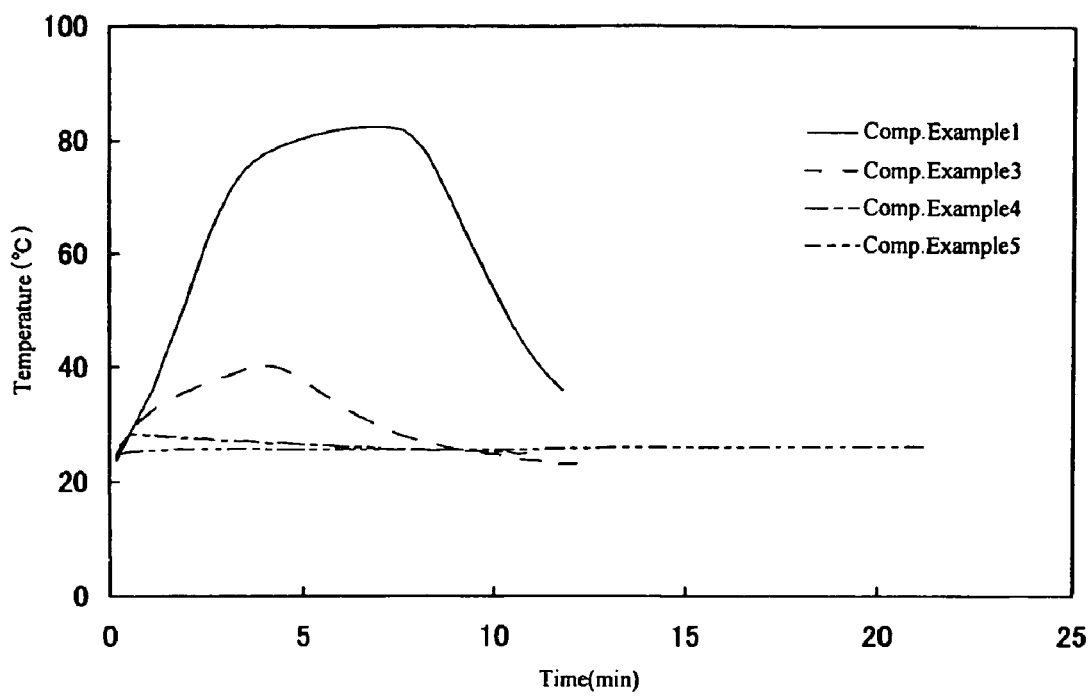
FIG. 3 is a graph of the heat generation characteristics observed in Comparative Examples.
Figure 4:
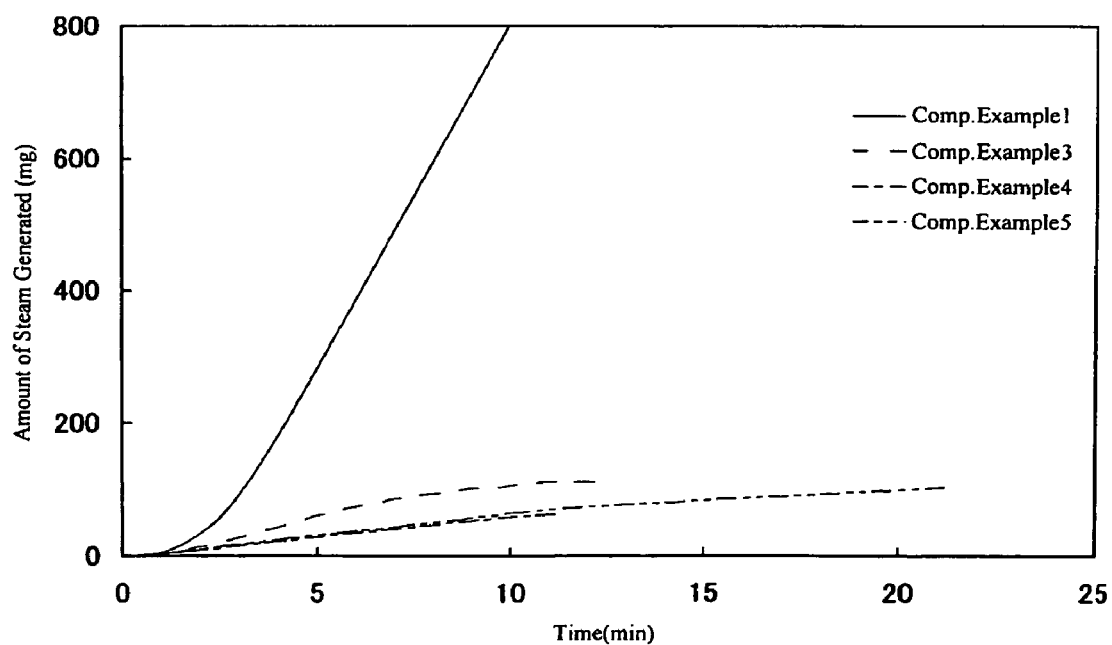
FIG. 4 is a graph representing the steam generation characteristics in Comparative Examples.

As is shown in Table 2, the molded sheets obtained in Examples were thin and yet tearproof. As shown in Table 3 and FIG. 1, all the heat generating sheets prepared by using these molded sheets exhibited superior heat generation characteristics, that is, they reached high temperatures and maintained temperatures of 40° C. or higher for at least one minute. Most of the heat generating sheets generated more than 100 mg of steam as is seen from Table 3 and FIG. 2. Furthermore, they had high flexibility even after heat generation reaction. In contrast, the heat generating sheets obtained in Comparative Examples 1 and 3 to 5 had the following defects as proved in Tables 2 and 3 and FIGS. 3 and 4. In Comparative Example 1, although the heat generating sheet was equal to Examples in heat and steam generation characteristics, the molded sheet was so brittle that it broke easily and had poor molding properties. In Comparative Example 2, the molding properties were so poor, resulting in difficulty of sheet forming. The heat generating sheets of Comparative Examples 3 to 5 were inferior in both heat generation characteristics and steam generation characteristics. In particular, Comparative Examples 3 and 4 showed poor molding properties.

INDUSTRIAL APPLICABILITY

The present invention provides a heat generating sheet excellent in not only conformability to a part of a body or a container but fabricability and productivity, a method of producing the heat generating sheet, a molded sheet used in the production of the heat generating sheet, and a method of producing the molded sheet.

The invention claimed is:

1. A molded sheet containing at least an oxidizable metal, a moisture retaining agent, and a fibrous material and having a content of components other than the fibrous material of 50% by weight or higher, a thickness of 0.08 to 1.2 mm, and a breaking length of 100 to 4000 m.

2. The molded sheet according to claim 1, wherein the breaking length is 200 to 4000 m.

3. The molded sheet according to claim 1, wherein the fibrous material has a CSF of 600 ml or less.

4. A heat generating sheet comprising the molded sheet of claim 1, the molded sheet being impregnated with an electrolyte solution.

5. The heat generating sheet according to claim 4, which is made up of a stack of at least two of the molded sheets.

6. The heat generating sheet according to claim 4, which is covered with a cover layer having oxygen permeability.

7. The molded sheet according to claim 1, wherein the breaking length is 100 to 1555 m.

8. A molded sheet containing at least an oxidizable metal, a moisture retaining agent, and a fibrous material and having a content of components other than the fibrous material of 50% by weight or higher, a thickness of 0.08 to 1.2 mm, and a breaking length of 100 to 4000 m, wherein said molded sheet is free of electrolytes and wherein said molded sheet is dried by heating.

9. The molded sheet according to claim 8, wherein the breaking length is 200 to 4000 m.

10. The molded sheet according to claim 8, wherein the fibrous material has a CSF of 600 ml or less.

11. A heat generating sheet comprising the molded sheet of claim 8, the molded sheet being impregnated with an electrolyte solution.

12. The heat generating sheet according to claim 11, which is made up of a stack of at least two of the molded sheets.

13. The heat generating sheet according to claim 11, which is covered with a cover layer having oxygen permeability.

14. A method of producing a molded sheet comprising the steps of forming a wet web by a papermaking process using a raw material composition containing at least an oxidizable metal, a moisture retaining agent, and a fibrous material, dewatering the wet web, and drying the wet web, wherein said molded sheet has a content of components other than the fibrous material of 50% by weight or higher, a thickness of 0.08 to 1.2 mm, and a breaking length of 100 to 4000 m.

15. A method of producing a heat generating sheet including the step of impregnating a molded sheet with a solution of an electrolyte, the molded sheet being the molded sheet produced by the method according to claim 14.

16. The method of producing a heat generating sheet according to claim 15, wherein the step of impregnating with a solution of an electrolyte is preceded or followed by the step of stacking two or more of the molded sheets.

17. The method of producing a molded sheet according to claim 14, wherein the fibrous material has a CSF of 600 ml or lower.

18. A method of producing a molded sheet comprising the steps of forming a wet web by a papermaking process using a raw material composition containing at least an oxidizable metal, a moisture retaining agent, and a fibrous material, wherein said molded sheet is free from electrolytes, dewatering the wet web, and drying the wet web, wherein said molded sheet has a content of components other than the fibrous material of 50% by weight or higher, a thickness of 0.08 to 1.2 mm, and a breaking length of 100 to 4000 m.

19. A method of producing a heat generating sheet including the step of impregnating a molded sheet with a solution of an electrolyte, the molded sheet being the molded sheet produced by the method according to claim 18.

* * * * *